US009695882B2

(12) United States Patent
Jakoubek

(10) Patent No.: US 9,695,882 B2
(45) Date of Patent: Jul. 4, 2017

(54) TORQUE LIMITING DEVICE

(71) Applicant: Jakoubek Medizintechnik GmbH, Liptingen (DE)

(72) Inventor: Franz Jakoubek, Liptingen (DE)

(73) Assignee: JAKOUBEK MEDIZINTECHNIK GMBH, Liptingen (DE)

( * ) Notice: Subject to any disclaimer, the term of this patent is extended or adjusted under 35 U.S.C. 154(b) by 0 days.

(21) Appl. No.: 14/635,384

(22) Filed: Mar. 2, 2015

(65) Prior Publication Data

US 2015/0252855 A1   Sep. 10, 2015

Related U.S. Application Data

(60) Provisional application No. 61/950,286, filed on Mar. 10, 2014.

(30) Foreign Application Priority Data

Nov. 5, 2014   (EP) .................................. 14003716

(51) Int. Cl.
| F16D 7/04 | (2006.01) |
| B25B 23/142 | (2006.01) |
| B25B 23/00 | (2006.01) |
| B25B 23/14 | (2006.01) |
| A61B 90/00 | (2016.01) |

(52) U.S. Cl.
CPC .............. *F16D 7/048* (2013.01); *A61B 90/03* (2016.02); *B25B 23/0035* (2013.01); *B25B 23/141* (2013.01); *B25B 23/1427* (2013.01); *A61B 2090/031* (2016.02)

(58) Field of Classification Search
CPC ... F16D 7/048; A61B 90/03; A61B 2090/031; B25B 23/141; B25B 23/0035; B25B 23/1427
USPC .................. 464/37, 41; 81/475; 16/DIG. 41
See application file for complete search history.

(56) References Cited

U.S. PATENT DOCUMENTS

| 2,558,158 A * | 6/1951 | Rock ................... B25B 23/1427 |
| | | 464/37 X |
| 2,773,370 A * | 12/1956 | Intraub ..................... F16D 7/10 |
| | | 464/37 X |
| 4,878,880 A * | 11/1989 | Williams ................ F16D 7/048 |
| | | 464/37 |
| 5,346,022 A * | 9/1994 | Krivec ................ B25B 23/1405 |
| | | 464/37 X |
| 5,746,298 A * | 5/1998 | Krivec ................... B25B 15/02 |
| | | 81/475 X |
| 7,467,576 B2 | 12/2008 | Gao |
| 7,621,815 B2 * | 11/2009 | Bosserdet, Jr. ......... F16D 7/048 |
| | | 464/37 |

FOREIGN PATENT DOCUMENTS

WO    WO 01/19571    3/2001

* cited by examiner

*Primary Examiner* — Gregory Binda
(74) *Attorney, Agent, or Firm* — Shlesinger, Arkwright & Garvey LLP

(57) ABSTRACT

A torque limiting device includes a handle; a drive shaft attached to the handle; a torque limiting assembly coupled to the drive shaft; the torque limiting assembly further including a shaft element; a first transmission member housing the shaft element; a second transmission member, the second transmission member being fixed to the shaft element and interacting with the first transmission member.

10 Claims, 11 Drawing Sheets

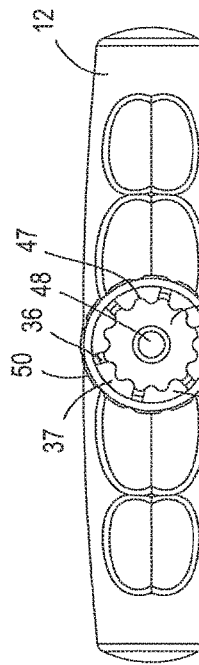
FIG. 2
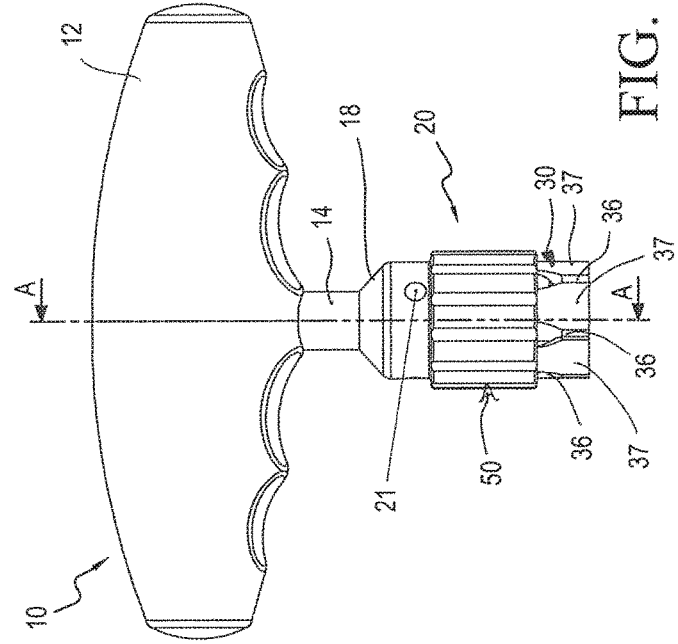
FIG. 3
FIG. 1
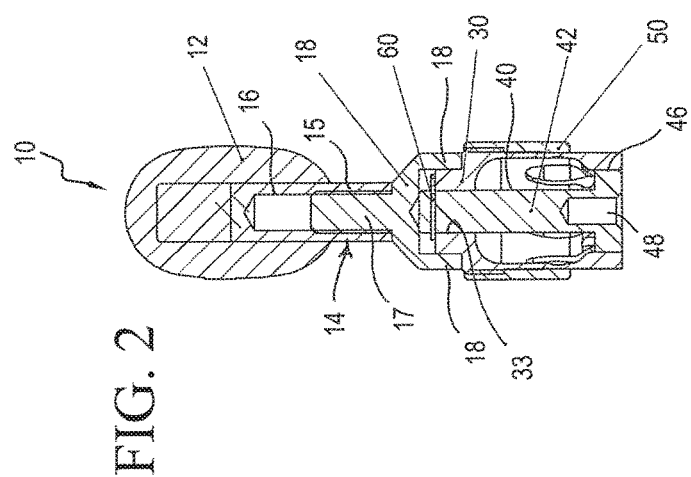

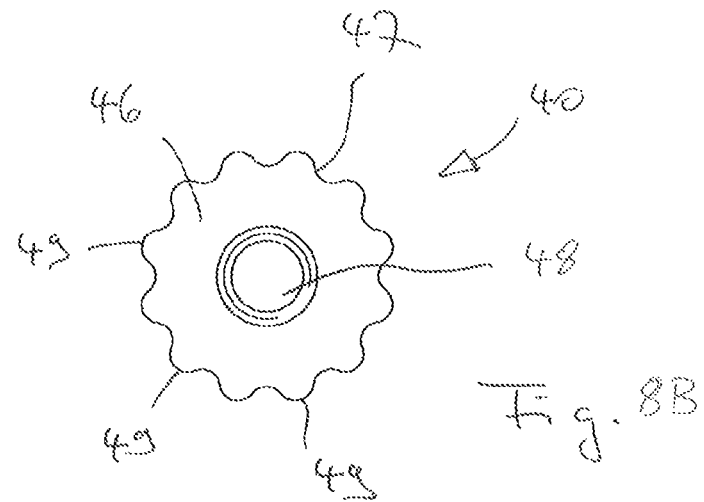
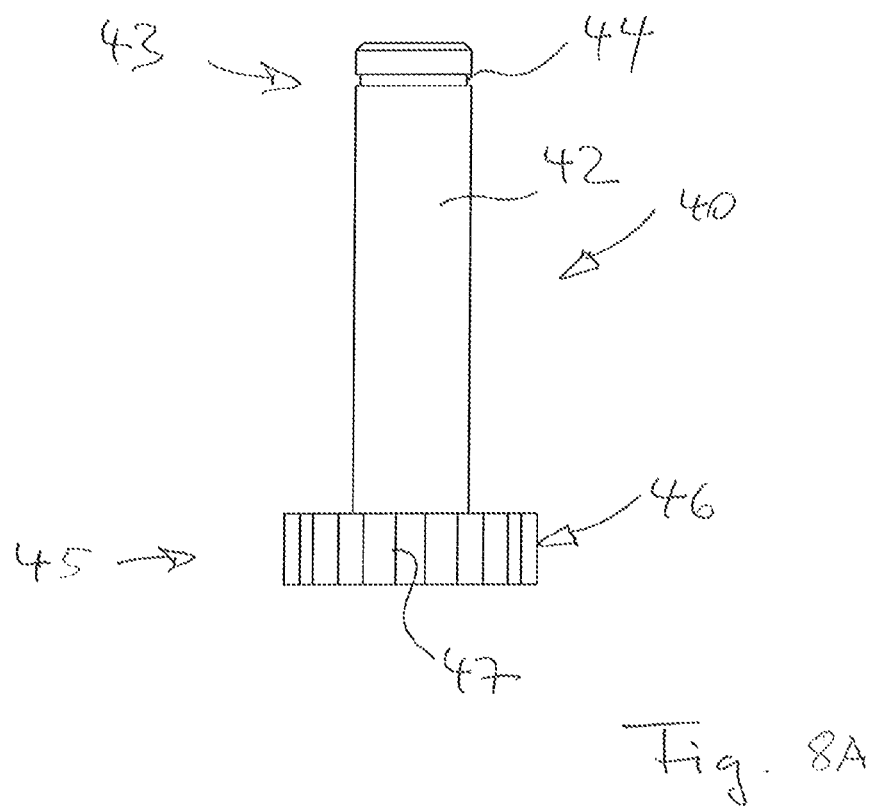

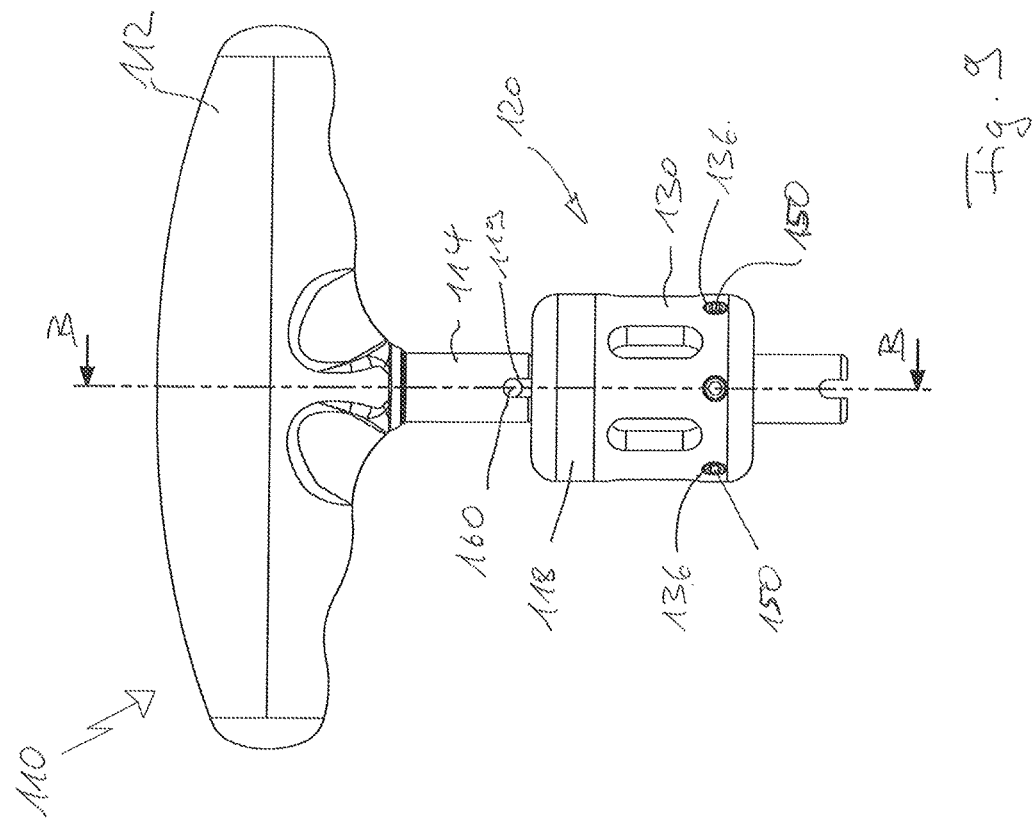
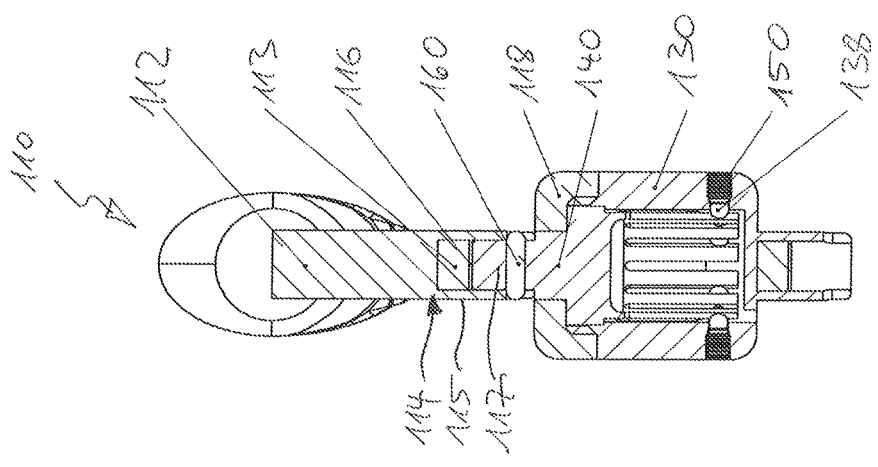

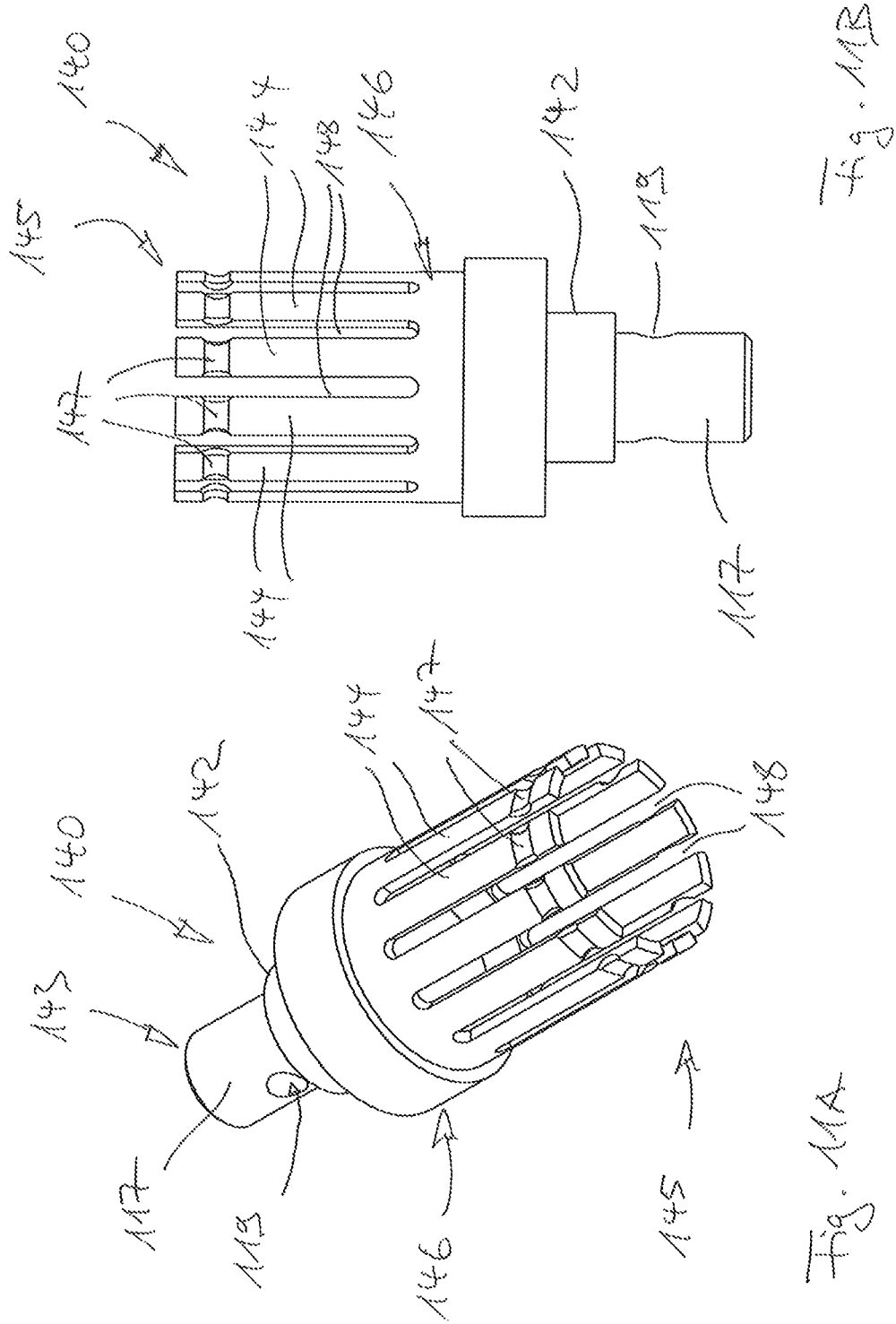

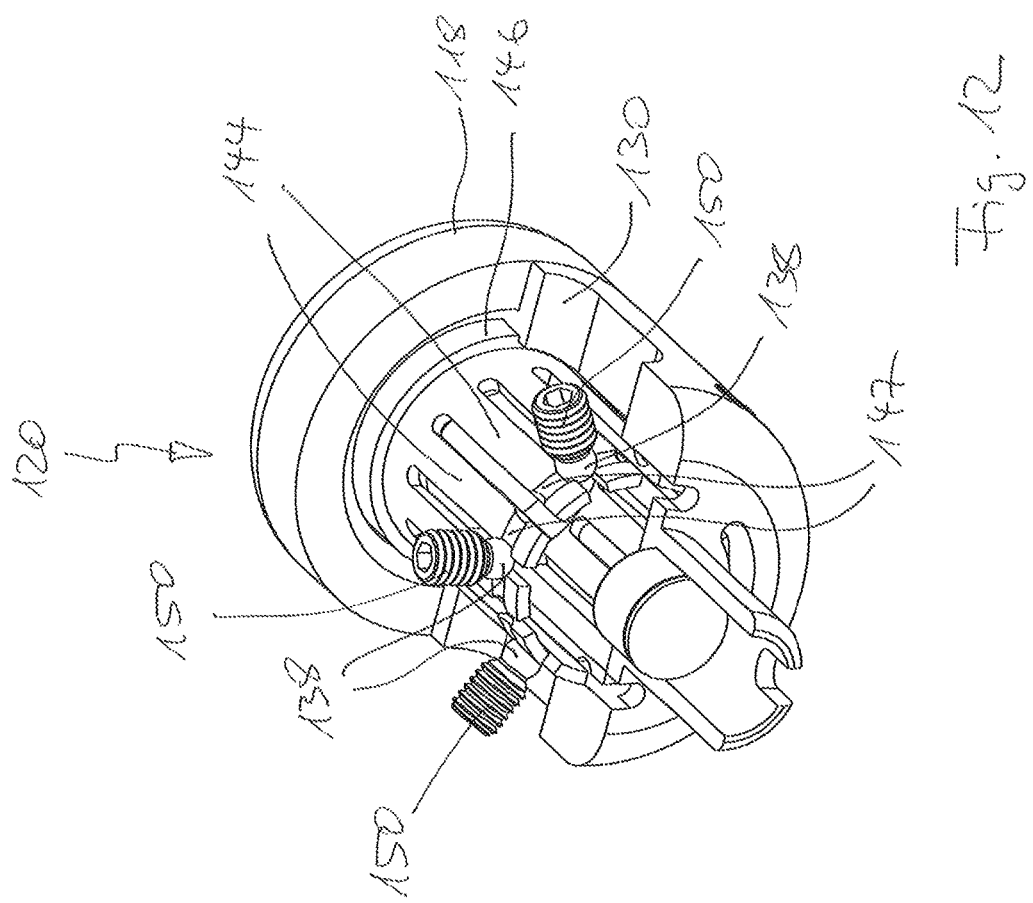

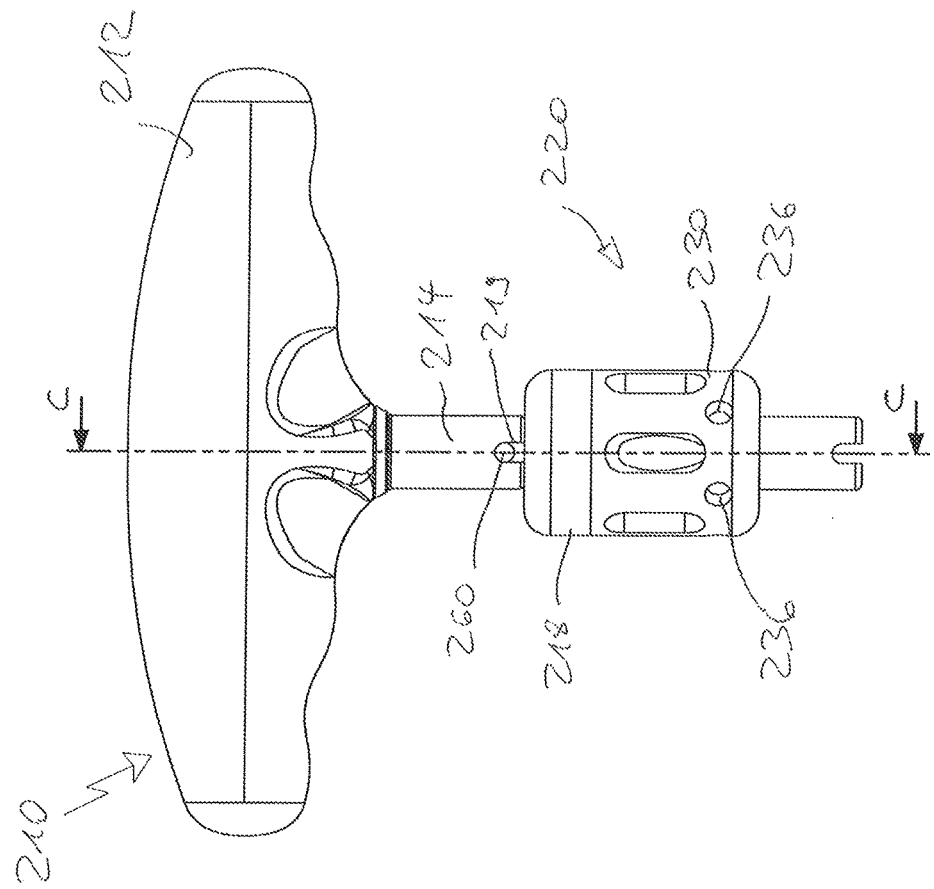
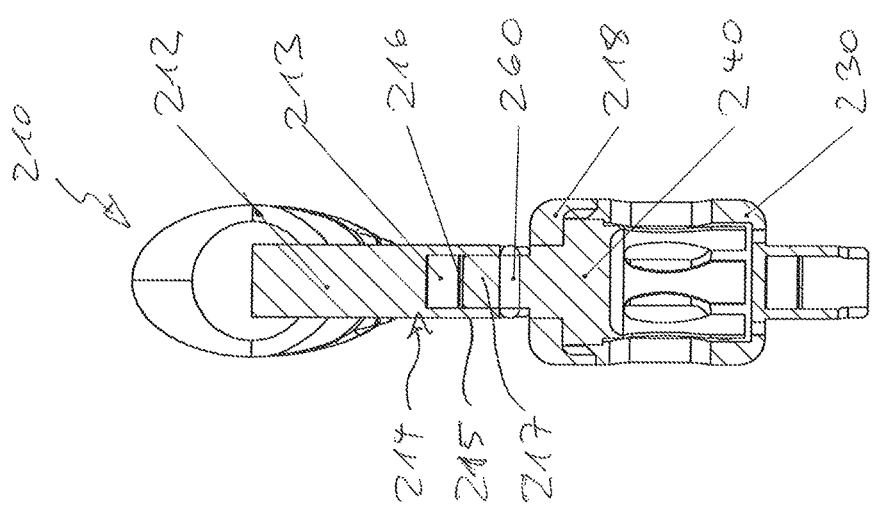
Fig. 13
Fig. 14

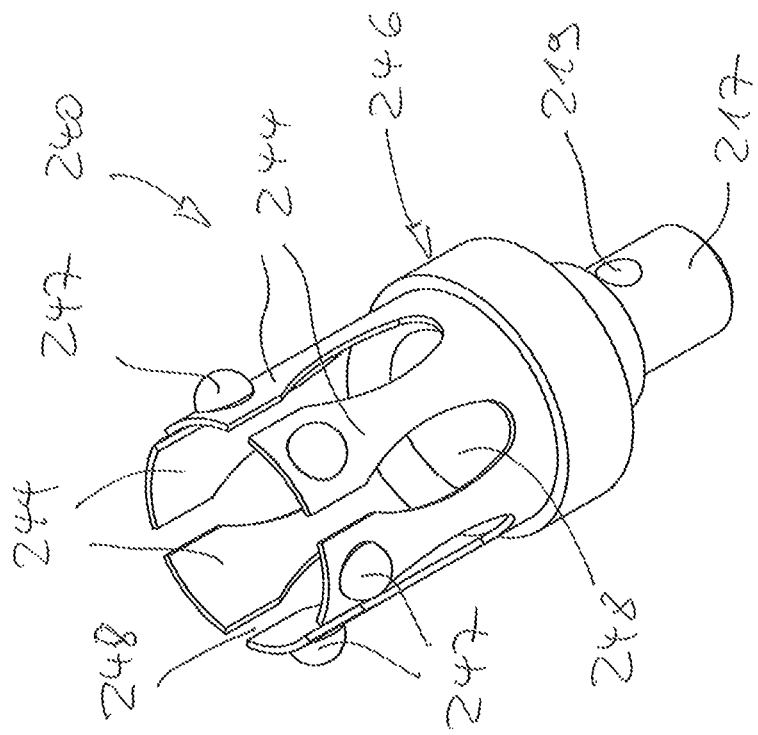
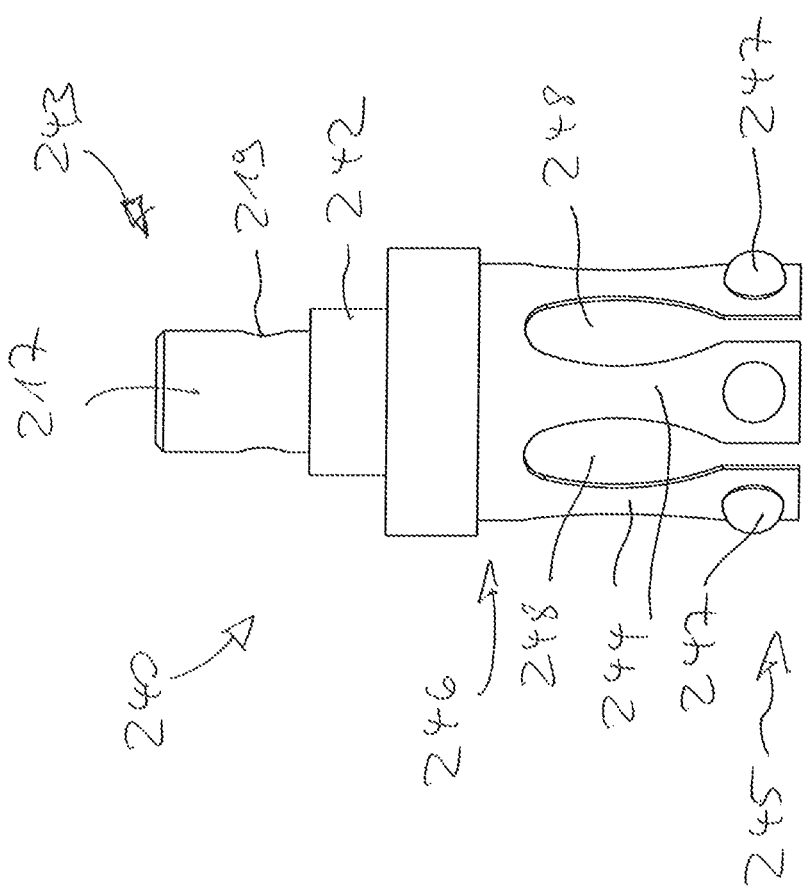

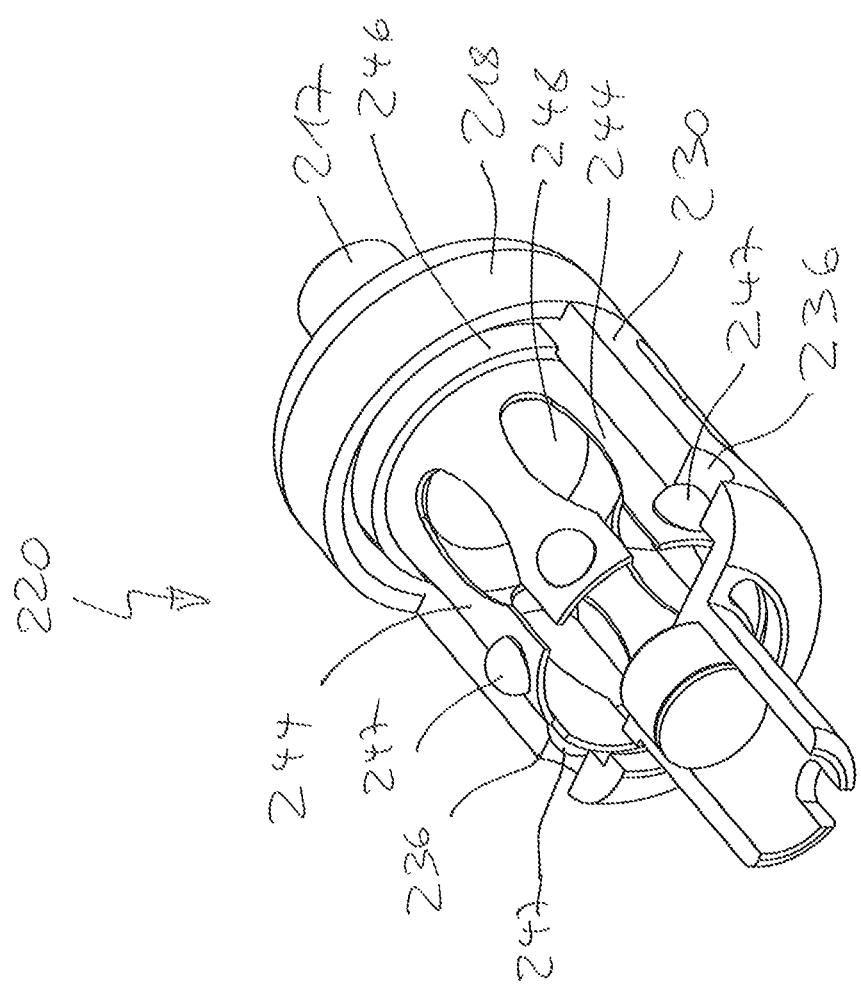

TORQUE LIMITING DEVICE

RELATED APPLICATIONS

This is a nonprovisional application of Provisional Application No. 61/950,286, filed on Mar. 10, 2014, which is hereby incorporated by reference.

This a nonprovisional application claiming the priority benefit of EP 14 003 716.9, filed on Nov. 5, 2014, which is hereby incorporated by reference.

TECHNICAL FIELD

The present invention relates to mechanical drive devices, and, more specifically, to drive devices that will limit the torque being delivered from the device. The present invention particularly relates to a device for adjusting and limiting the amount of torque in medical devices and in surgical or neurosurgical use.

DESCRIPTION OF THE RELATED ART

U.S. Pat. No. 7,467,576 B2 discloses a clutch assembly for use with a torque limiting driver. The clutch assembly comprises two relatively rotatable clutch plates, a driving plate and a camming plate, that face one another, with a plurality of rolling members housed between the two members. When the rolling members are in the override position, the recesses form individual housings for the rolling members that include a gap located between the rolling members and a respective curvilinear base area of the drive plate. The clutch assembly is secured to a drive shaft by a pin, which is supported by a pair of wheels located on opposing sides of the pin.

WO 01/19571 A1 discloses a torque-limiting device for surgical use, comprising a rotatable housing, a base unit engaged within the first end of the housing, and having an input stem for engagement with a rotary device. An output shaft extends through the second end of the housing, and a flange is disposed about the shaft, whereby flange and base unit have adjacent faces. A plurality of recesses are provided in the faces of the base unit and the flange, the recesses being positionable for mutual alignment, and a ball is located in and between each pair of the opposing recesses. An elastic element is disposed about the output shaft between the flange and the second opposing end of the housing, the elastic element exerting a force to maintain a drive connection between the balls and the opposing faces, the drive connection being severed when the torque exerted on the balls by the elastic element is exceeded by the counter-torque exerted on the balls by the flange.

SUMMARY OF THE INVENTION

In contrast thereto, the invention provides a torque limiting device with the features as disclosed herein.

The present invention provides a torque limiting device comprising a handle, a drive shaft attached to the handle and a torque limiting assembly coupled to the drive shaft. The torque limiting assembly further comprises a shaft element having a profiled member and a first transmission member housing the shaft element. Further, the torque limiting assembly comprises a second transmission member which is fixed to the shaft element and interacts with the first transmission member.

The torque limiting assembly may also comprise an adjusting member or adjusting means surrounding the first transmission member, the adjusting means being designed to adjust the degree of interaction between the first transmission member and the second transmission member.

The gist of the present invention consists in the idea to provide two profiles of a first and a second transmission member, respectively, camming with each other along a contact surface in such a manner that a flexible part of one of the profiles is urged out of contact once the torque to be transmitted exceeds a given threshold, thus slipping over a given protrusion and bending back after that protrusion thus resulting in a camming relative movement. As a result, even if the handle is continued to be rotated, this rotating movement will not be further transmitted between the first and the second transmission members once the flexible profile portion starts to be urged away from contact when a predetermined torque has been reached.

Further features and embodiments of the invention will become apparent from the description and the accompanying drawings.

It will be understood that the features mentioned above and those described hereinafter can be used not only in the combination specified but also in other combinations or on their own, without departing from the scope of the present invention.

The invention is schematically illustrated in the drawings by means of an embodiment by way of example and is hereinafter explained in detail with reference to the drawings. It is understood that the description is in no way limiting on the scope of the present invention and is merely an illustration of a preferred embodiment of the invention.

BRIEF DESCRIPTION OF THE DRAWINGS

FIG. 1 is a side elevation view of an embodiment of a torque limiting device of the invention.

FIG. 2 is a cross-sectional view of the torque limiting device taken along the line A-A of FIG. 1.

FIG. 3 is a bottom elevation view of the torque limiting device of FIG. 1.

FIG. 8A is a side elevation view of the shaft element of the torque limiting assembly of FIG. 5.

FIG. 8B is a bottom elevation view of the shaft element of FIG. 8A.

FIG. 9 is a side elevation view of another embodiment of a torque limiting device of the invention.

FIG. 10 is a cross-sectional view of the torque limiting device taking along the line B-B of FIG. 9.

FIG. 11A is a side elevation view of the shaft element of the torque limiting device of FIG. 10.

FIG. 11B is a perspective view of the shaft element of FIG. 11A.

FIG. 12 is a perspective view of the torque limiting assembly in partly cutaway view of the torque limiting device of FIG. 10.

FIG. 13 is a side elevation view of still a further embodiment of a torque limiting device of the invention.

FIG. 14 is a cross-sectional view of the torque limiting device taken along the line C-C of FIG. 1.

FIG. 15A is a side elevation view of the shaft element of the torque limiting device of FIG. 14.

FIG. 15B is a perspective view of the shaft element of FIG. 15A.

FIG. 16 is a perspective view of the torque limiting assembly in party cutaway view of the torque limiting device of FIG. 14.

DETAILED DESCRIPTION

Figure 4:
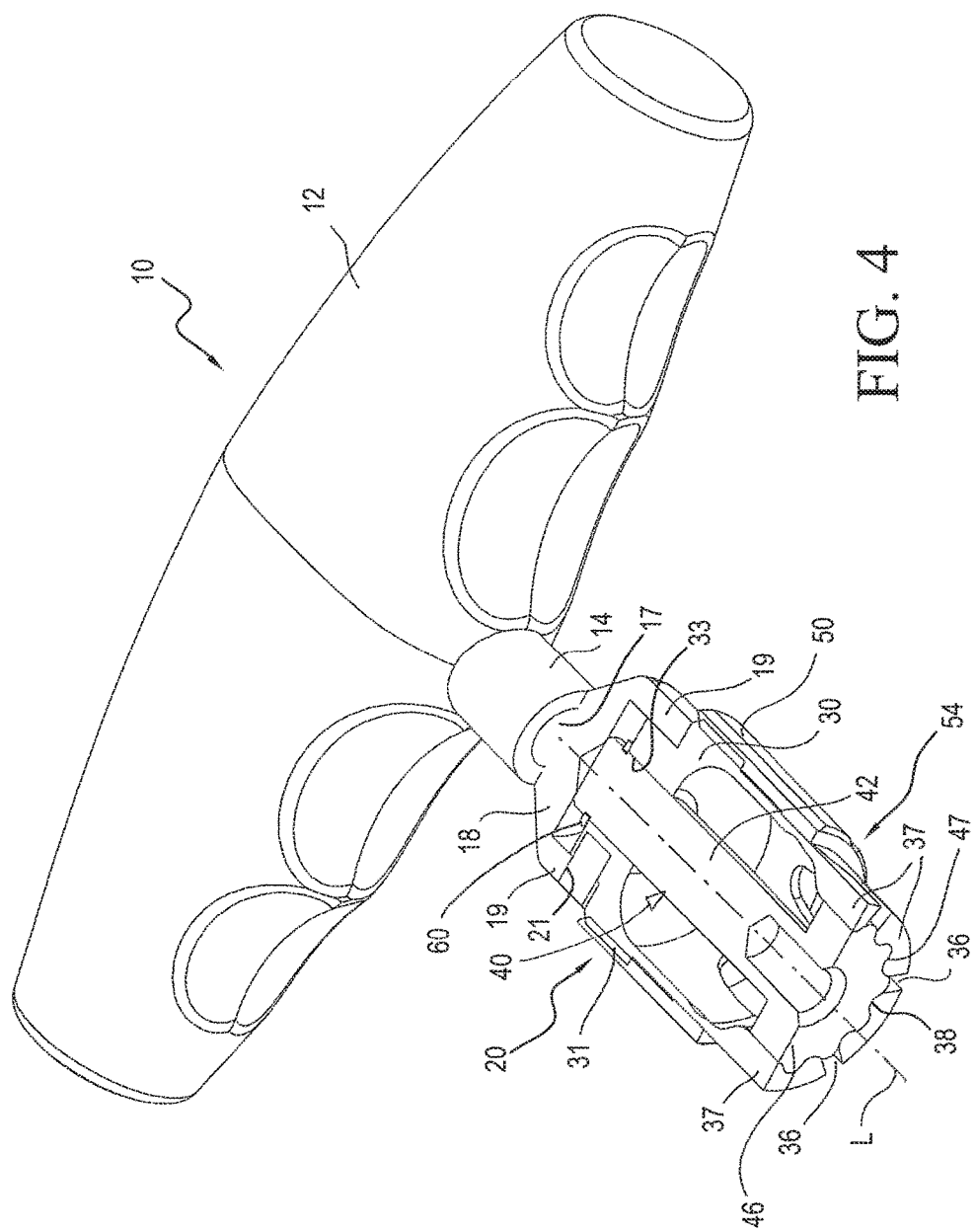
FIG. 4 is a perspective view of the torque limiting device of FIG. 1 with its torque limiting assembly in partly cutaway view.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims. In the following description, same or like features are designated with the same reference numerals or by the same reference numerals increased by 100 or 200, respectively.

FIG. 1 is a side elevation view of a torque limiting device 10 in accordance with the invention, and FIG. 2 shows a cross-sectional view of the torque limiting device 10, taken along the line A-A of FIG. 1, and FIG. 3 shows a bottom elevation view of the torque limiting device 10.

With reference to FIGS. 1 to 3, the torque limiting device 10 generally comprises a handle 12 and a drive shaft 14 attached to the handle 12. The handle 12 may be a silicone handle, and the drive shaft 14 may for example consist of a T-section steel core extending outside of the handle 12 with one of its webs 15, which web 15 has an internal thread 16.

The torque limiting device 10 further comprises a torque limiting assembly, generally depicted with reference numeral 20. A partly cutaway view of the torque limiting assembly is shown in FIG. 4. The torque limiting assembly 20 is coupled to the drive shaft 14 by means of an intermediate element 18. The intermediate element 18 has a generally Y-shaped cross section with a first single leg 17 and two opposing legs 19. The first leg 17 has an outer thread being inserted into the inner thread 16 of the drive shaft 14. The opposing two legs 19 of the intermediate element 18 form an opening designed to house the torque limiting assembly 20.

The torque limiting assembly 20 generally comprises the following elements, a first transmission member 30, a second transmission member 46, a shaft element 40, and an adjusting member 50.

In the embodiment illustrated in the FIGS. 1 to 8 and described herein, the first transmission member is designed to be an expansion sleeve 30, and the adjusting means is designed to be an adjusting sleeve 50 surrounding the inner expansion sleeve 30.

In more detail, the expansion sleeve 30 has a generally hollow cylindrical shape with a first end 32 and a second end 34. The first end 32 of the expansion sleeve 30 faces towards the handle 12 whereas the opposing end 34 faces away from the handle 12. The expansion sleeve 30 further comprises a plurality of slots 36 starting at the second end 34 and extending along the lateral cylindrical surface of the expansion sleeve 30 for a certain length in order to define a plurality of legs 37 between the slots 36. Due to the gaps between the legs 37, the legs 37 can move to a certain degree radially in a flexible manner. They can be slightly bent outwardly (as well as inwardly).

In the depicted embodiment, the shape of the slots 36 is substantially straight at the second end 34 and gradually enlarges in the direction of the first end 32 where the slots have some kind of drop shape. The smaller gap of the straight portion of the slots 36 at the second end 34 ensures a larger contact surface of the legs 37 with the second transmission element 46, increasing the repeating accuracy for the torque. The drop or arcuate shape creates a larger distance between the neighbouring legs and ensures the elasticity of the legs 37 as well as the endurance/durability.

Figure 5:
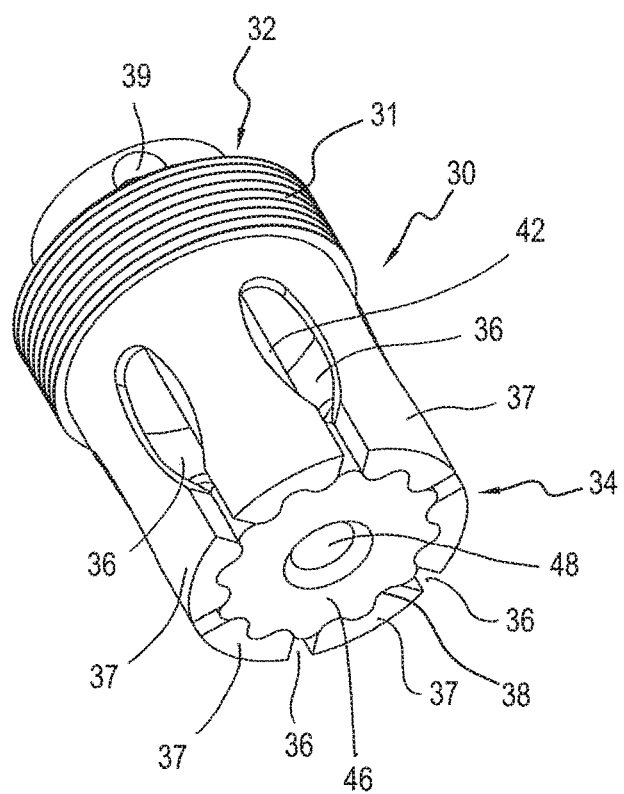
FIG. 5 is a perspective view of the expansion sleeve of the torque limiting assembly of the torque limiting device of FIG. 1 with inserted shaft element.
Figure 7:
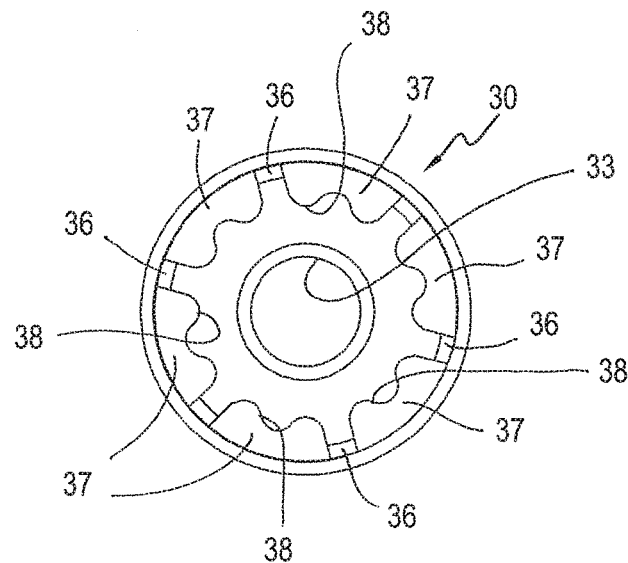
FIG. 7 is a bottom elevation view of the expansion sleeve of FIG. 6.
Figure 6:
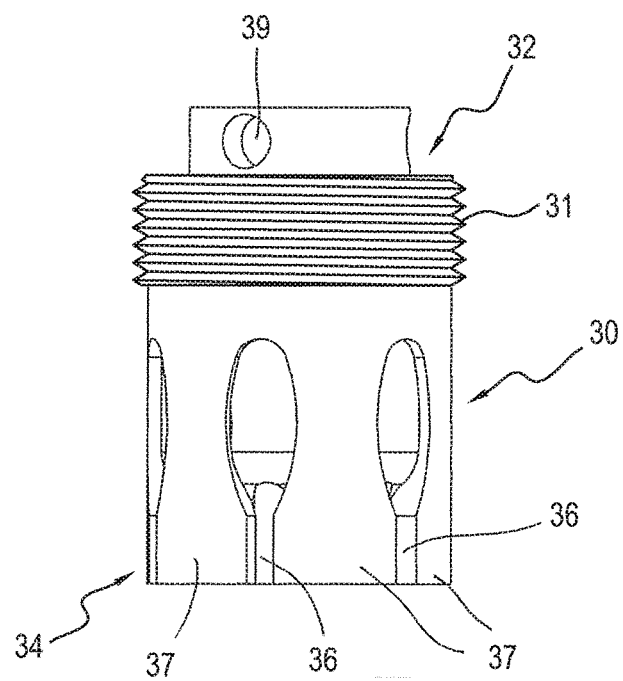
FIG. 6 is a side elevation view of the expansion sleeve of FIG. 5 without inserted shaft element.

The inner circumference of the legs 37 at the second end 34 has a profiled shape 38, as can be seen from FIGS. 4 and 5, for example. The profiled shape 38 may be a sinusoidal curve profile or a knurling, or the like, with rounded protrusions. The material of the expansion sleeve 30 is chosen from a group of materials that ensure both adequate elasticity and endurance (in order to avoid fatigue), this group covering materials such as steel, stainless steel, high-grade or premium steel, highly tempered steel, or other comparable materials.

Towards the first end 32 of the expansion sleeve 30, the expansion sleeve 30 comprises a section of larger diameter on which an outer thread 31 is provided. The function of this thread 31 is explained in more detail below in connection with the adjusting sleeve 50.

The shaft element 40 comprises a shaft portion 42 of generally cylindrical form having a longitudinal axis L. The shaft element 40 comprises a first end 43 and a second end 45, the first end 43 comprising an annular groove 44. At its second end 45, the shaft element 40 has a generally cylindrical enlargement portion 46 having a larger diameter than the shaft portion 42. The enlargement portion is formed integrally with the shaft element 40 and serves as the second transmission member of the invention. Of course, the second transmission member 46 may also be formed separately from the shaft element.

The shaft element 40 is designed in such a manner that it fits within the expansion sleeve 30, with its first end 43 expanding into an opening 33 at the first end 32 of the expansion sleeve 30 where it can be secured by means of a retaining ring 60 engaging with the groove 44.

The second transmission member 46 comprises, at its outer peripheral surface, a profile 47 which is designed to be complementary with the profile 38 of the legs 37, i.e. a sinusoidal or knurled profile with protrusions 49. The second transmission member 46 on the opposing second end 45 of the shaft element 40 thus comes into complementary engagement with the inner circumferential profile 38 of the legs 37 of the expansion sleeve 30. Of course, the second transmission member 46 can have a different shape and/or a different position and must not be located at the second end 45 of the shaft element 40.

The outer adjusting sleeve 50 is slipped over the inner expansion sleeve 30 where it can be adjusted in its position and fixed along the axial direction of the expansion sleeve 30. Adjustment of the outer sleeve 50 may be done by means of a suitable inner thread for engagement with the thread 31 on the expansion sleeve 30 as mentioned above. The inner and outer threads may be designed to provide a rather tight connection between the expansion sleeve and the adjusting sleeve so that, once the adjusting sleeve has been set to a certain desired torque, the sleeves cannot move relatively to each other. Another embodiment may provide, alternatively or additionally, for a set screw (not shown) to secure the adjusting sleeve at the desired location. Another embodiment is designed to be set to a desired torque for a specific application (which will remain the same torque not to be altered) and then secured permanently by means of an appropriate adhesive or soldering or the like.

The larger the distance between the area covered by the adjusting sleeve 50 and the second end 34 of the expansion sleeve 30, the more room to move is available for the flexible legs 37 to move outwardly. The more the adjusting sleeve 50 approaches the second end 34 of the expansion sleeve 30, the less this room to move becomes and the expansion sleeve 30 will become more rigid. Thus, the length of the exposed legs 37 is a factor to determine the desired torque. If the adjusting sleeve covers the expansion sleeve all the way to its second end 34, there will be an unlimited torque.

For assembly, the shaft element 40 is inserted into the expansion sleeve 30 through an opening from the second end 34 in coaxial manner and by putting the first end 43 of the shaft element 40 through the upper opening 33 of the expansion sleeve 30 where the shaft element 40 is then fixed by the retaining ring 60. It is to be noted that the retaining ring 60 does not provide for an angular fixation between the expansion sleeve 30 and the shaft element 40. At the lower end, i.e. the second ends 34, 45 of the expansion sleeve 30 and the shaft element 40, respectively, the enlargement portion 46 mates with its circumferential profile 47 with the complementary profile 38 of the legs 37.

Next, the adjusting sleeve 50 is slipped over the expansion sleeve 30 in coaxial manner, and the resulting torque limiting assembly 20 is inserted with the first end 42 first into the intermediate element 18 in order to be coupled to the drive shaft 14 of the handle 12. In order to obtain an angular fixation between the intermediate element 18 and the torque limiting assembly 20, at least one pair of mating holes or apertures 21 and 39 are provided in the intermediate element 18 and the upper end 32 of the expansion sleeve 30, respectively, through which, when superimposed or aligned, a suitable pin (not shown) may be inserted and sealed. In one example, three pairs of mating holes may be provided equidistantly at 120 degrees.

At the lower or second end 45 of the shaft element 40, an opening 48 is provided as a coupling element for insertion of an appropriate tool. For example, the hole 48 may be designed to be a so-called AO coupling.

In operation, the tool inserted in the coupling element 48 is set on a screw or the like in order to fasten that screw by turning the handle 12 in the appropriate direction. By doing so, a torque is transmitted due to the angular movement of the handle 12 which is transmitted via drive shaft 14 and intermediate element 18 to expansion sleeve 30 (first transmission member) and from the expansion sleeve 30 onto the second transmission member 46 via the mating profiles 38, 47 and thus the shaft element 40 fixedly connected to the second transmission member 46.

Once the torque to be transmitted exceeds a given threshold (which is defined by positioning the adjusting sleeve 50 in an appropriate distance to the second end 45), the transmission of the angular movement from the expansion sleeve 30 to the shaft element 40 is disrupted as the legs 37 will be urged outwardly by the protrusions 49 of the profile 47, thus slipping over a given protrusion and bent back inwardly after that protrusion, thus resulting a camming relative movement (why the second transmission member may also be called a camming member). As a result, even if the handle 12 is continued to be rotated, this rotating movement will not be further transmitted from the expansion sleeve to the shaft element 40 once the legs 37 start to "expand" outwardly once a predetermined torque has been reached.

FIG. 9 shows a side elevation view of another embodiment of a torque limiting device 110 in accordance with the invention, and FIG. 10 shows a cross-sectional view of the torque limiting device 110, taken along the line B-B of FIG. 9.

The torque limiting device 110 generally comprises a handle 112 and a drive shaft 114 attached to the handle 112. Again, the handle 112 may be a silicon handle, and a drive shaft 114 may for example consist of a T-section steel core extending outside of the handle 112 with one of its webs 115.

The torque limiting device 110 further comprises a torque limiting assembly, generally depicted with reference numeral 120. A partly cutaway view of the torque limiting assembly 120 is shown in FIG. 12.

The torque limiting assembly 120 is coupled to the drive shaft 114 by means of a magnetic element 113 placed into a recess of the web 115 of the drive shaft 114, covered by a plate 116 fixedly positioned in the recess, e.g. by means of adherence, bonding, soldering, welding etc. The magnetic element 114 is strong enough to hold an upper leg 117 extending out of the torque limiting assembly 120, which leg 117 is of an appropriate magnetisable material. The described magnetic connection between the handle 112 and the torque limiting assembly 120 can be easily detached such that different torque limiting assemblies can be connected with a given handle in a very fast and reliable matter. An intermediate sleeve 118 covers the upper portion of the shaft element 140 beneath the junction to the drive shaft 114.

The torque limiting assembly 120 generally comprises the following elements: a first transmission member 130, a second transmission member 146, a shaft element 140, and an adjusting means 115.

The principle already shown and explained above in connection with the first embodiment, namely that a first transmission member and a second transmission member are in mating contact with correlating profiles with a resulting camming relative movement (at least one of the profiles being flexible) is reversed in this second embodiment.

In the second embodiment shown in the FIGS. 9 to 12, the first transmission member 130 is a solid sleeve having a generally cylindrical hollow shape, housing in its hollow cavity the shaft element 140. The shaft element 140 comprises at its first end 143 the extending leg 117 for attachment with the handle 112, and at its second end 145 facing away from the handle a second transmission member 146 attached to a shaft portion 142 of the shaft element 140. The shaft element 140 together with the second transmission member 146 may for example be made in one integral piece, or in two pieces fixedly attached to each other. Extending from its lower end (in the depiction of FIGS. 9 and 10) the first transmission member 130 comprises a coupling element for insertion of an appropriate tool.

The second transmission member 146 has a generally hollow cylindrical shape, the sleeve of which comprises a plurality of longitudinal parallel legs 144 with gaps 148 therebetween. The legs 144 are flexible as described above with regard to the legs 37 of the expansion sleeve 30, and can be bent inwardly as well as outwardly. In the area adjacent to the second end 145 of the shaft element 140, the legs 144 comprise notch-like recesses 147 with rounded bottoms.

As already described, the first transmission member 130 comprises a solid sleeve extending around the shaft element 140. The first transmission member 130 also comprises a plurality of threaded through-holes 136 with grub screws or threaded pins 150 inserted therein. Further, balls 138 are inserted in the threaded through-holes 136 before the respective grub screw 150 is screwed into each of the through-holes 136 such that the balls 138 somewhat extend into the inner cavity of the first transmission member 130, projecting into the notch-like recesses 147 of the legs 144 of the second transmission member 146.

The grub screws 150 as described above are designed to adjust the degree of projection/protrusion of the balls 138 into the recesses 147. Thus, the grub screws 150 have the function of adjusting means or adjusting member surrounding the first transmission member in this second embodiment. In the embodiment depicted in the FIGS. 9 to 12, grub screws 150 are evenly distributed along the circumference of the sleeve of the first transmission member at a distance of 60°, i.e. there are six grub screws, but any other suitable number of grub screws can be used to achieve the effect of the invention, as can be readily acknowledged by the person skilled in the art.

FIGS. 14 to 16 illustrate yet another embodiment of the torque limiting device of the invention, generally depicted by 210.

The basic design of the torque limiting device 210 according the third embodiment is very similar to the one of the second embodiment described with reference to FIGS. 9 to 12, and thus like features are designated with the same reference numeral increased by 100. For the description of the basic design of the torque limiting device 210 with handle and attachment of the handle, it is referred to the above description of the second embodiment.

The torque limiting assembly 220 of the third embodiment generally comprises a first transmission member 230, a second transmission member 246 and a shaft element 240. It is noted that the torque limiting assembly 220 of the third embodiment of the invention does not comprise an adjusting means, resulting in a torque limiting device with a fixed threshold torque. Such a device can be useful in certain application areas where a certain torque is needed and no variations from that torque are desired.

The first transmission member 230 is a solid sleeve having a generally cylindrical hollow shape housing in its hollow cavity the shaft element 240 together with the second transmission member 246.

At its second end 245 facing away from the handle, a second transmission member 246 attached to a shaft portion 242 of the shaft element 240 is provided.

The second transmission member 246 has a generally hollow cylindrical shape, the sleeve of which comprises a plurality of longitudinal parallel legs 244 with slots 248 therebetween. It is to be noted that the slots 248 between the legs 244 are similar to the slots 36 as shown in the first embodiment above, i.e. the shape of the slots 248 is substantially straight at the second end 245 and gradually enlarges in the direction of the first end 243 where the slots have some kind of drop shape. Again, according to the invention, due to the gaps between the legs 244 the legs 244 can move to a certain degree radially in a flexible manner. They can be slightly bent outwardly (as well as inwardly). The smaller gap of the straight portion of the slots 248 at the second end 245 ensures a larger contact surface of the legs 248 with the first transmission element 230, increasing the repeating accuracy for the torque. The drop or arcuate shape creates a larger distance between the neighbouring legs and ensures the elasticity of the legs as well as the endurance/durability.

In the area of the second end 245 the legs 244 comprise on their outer circumferential surface protrusions 247. The protrusions may have a generally semi-spherical shape as illustrated in the embodiments of FIGS. 15 and 16, but other suitable shapes may be adopted by the skilled person. In the shown embodiment, six protrusions are provided, i.e. one protrusion on each leg, but other designs can be contemplated by the person skilled in the art, such as for example more than one protrusion on each leg or fewer or more legs with one or more protrusions thereon.

When mounted, the shaft element 240 together with the second transmission member 246 fixedly attached thereto are housed within the hollow sleeve of the first transmission member 230 in such a manner that the protrusions project into holes 236 distributed radially on the sleeve of the first transmission member 230.

The protrusions 247 as described above provide for the profiled section of the second transmission member 246, and the holes 236 provide for the complimentary profiled section of the first transmission member 230. It is to be noted that there does not necessarily has to be one hole 236 for each protrusion 247; the invention would also work in case of more holes than protrusion or less holes than protrusions.

As already described above, the gist of the invention is to have two profiles of a first and a second transmission member, respectively, camming with each other along a contact surface in such a manner that a flexible part of one of the profiles (e.g. the legs) is urged away from the contact surface, i.e. outwardly or inwardly (depending on the design) once the torque to be transmitted exceeds a given threshold, thus slipping over a given protrusion and bending back after that protrusion thus resulting in a camming relative movement.

Different shapes and geometries of the various parts of the invention as shown and described above with the aid of the figures can be conceived by the skilled person. For example, the shape of the slots 36 can vary depending on the specific needs. All straight slots can be provided for example (as shown in connection with the second embodiment illustrated in FIGS. 9 to 12). The length of the adjusting sleeve can vary; while the adjusting sleeve of the shown embodiment does not cover the whole length of the expansion sleeve, other embodiments may provide a longer adjusting sleeve that would be able to cover the legs of the expansion sleeve in their entirety, thus providing for an unlimited torque. As seen in the third embodiment, the invention can be worked without provision of an adjusting means which results in a torque limiting device with a fixed threshold torque.

Various aspects of the invention cover the following:

1. A torque limiting device (10; 110; 210), comprising:
a handle (12; 112; 212);
a drive shaft (14: 114: 214) attached to the handle (12; 112; 212);
a torque limiting assembly (20; 120; 220) coupled to the drive shaft (14: 114: 214);
the torque limiting assembly (20; 120; 220) further comprising a shaft element (40; 140; 240);
a first transmission member (30; 130; 230) housing the shaft element (40; 140; 240);
a second transmission member (46; 146; 246), the second transmission member (46; 146; 246) being fixed to the shaft element (40; 140; 240) and interacting with the first transmission member (30; 130; 230).

2. The torque limiting device (10; 110; 210) of aspect 1, wherein the first transmission member (30; 130; 230) comprises a profiled section (38; 138; 238) which is in mating contact with a complimentary profiled section (47; 147; 247) of the second transmission member (46; 146; 246).

3. The torque limiting device (10; 110; 210) of aspect 2, wherein the profiled section (38, 47; 138, 147; 238, 247) of one of the first or the second transmission members (30, 46; 130, 146; 230, 246) comprises flexible portions (37; 144; 244) which slip or cam over the complimentary profiled section (38, 47; 138, 147; 238, 247) of the respective other one of the first or second transmission members (30, 46; 130, 146; 230, 246) once a predetermined torque has been reached.

4. The torque limiting device (10; 110) of any one of aspects 1 to 3, further comprising an adjusting member (50; 150) for adjusting the degree of interaction between the first transmission member (30; 130) and the second transmission member (46; 146).

5. The torque limiting device (10; 110) of aspect 4, wherein the adjusting member (50; 150) surrounds the first transmission member (30; 130).

6. The torque limiting device (10) of any one of aspects 1 to 5, wherein the first transmission member (30) is an expansion sleeve (30), and wherein the second transmission member (46) is a portion of a shaft element (40) housed within the expansion sleeve (30).

7. The torque limiting device (10) of aspect 6, wherein the expansion sleeve (30) comprises a first end (32) and a second end (34), and further comprises a plurality of legs (37) facing towards the second end (34) and being elastic radially with regard to an axis (L) of longitudinal extension of the expansion sleeve (30).

8. The torque limiting device (10) of aspect 6 or 7, wherein the second transmission member (46) is a camming member (46) interacting with the radially flexible legs (37) of the expansion sleeve (30).

9. The torque limiting device (10) of any one of aspects 4 to 8, wherein the adjusting member (50) is an adjusting sleeve (50) slipped over the expansion sleeve (30).

10. The torque limiting device (10) of aspect 9, wherein the adjusting sleeve (50) is rotatably adjustable on the expansion sleeve (30).

11. The torque limiting device (10) of aspect 10, wherein the adjusting sleeve (50) is rotatably mounted onto an outer thread on the expansion sleeve (30).

12. A torque limiting device, comprising:
a handle;
a drive shaft attached to said handle;
a torque limiting assembly coupled to said drive shaft;
said torque limiting assembly further comprising
a shaft element;
a first transmission member housing said shaft element;
a second transmission member, said second transmission member being fixed to the shaft element and interacting with said first transmission member; and
an adjusting member surrounding said first transmission member for adjusting the degree of interaction between said first transmission member and said second transmission member.

13. The torque limiting device of aspect 12, wherein the first transmission member is an expansion sleeve, and wherein the second transmission member is a portion of a shaft element housed within the expansion sleeve.

14. The torque limiting device of aspect 13, wherein the adjusting member is an adjusting sleeve slipped over the expansion sleeve.

15. The torque limiting device of aspect 13, wherein the expansion sleeve comprises a first end and a second end, and further comprises a plurality of legs facing towards the second end and being elastic radially with regard to an axis of longitudinal extension of the expansion sleeve.

16. The torque limiting device of aspect 13, wherein the second transmission member is a camming member.

17. The torque limiting device of aspect 14, wherein the adjusting sleeve is rotatably adjustable on the expansion sleeve.

18. The torque limiting device of aspect 17, wherein the adjusting sleeve is rotatably mounted onto an outer thread on the expansion sleeve.

19. The torque limiting device of aspect 12, wherein the first transmission member comprises a profiled section which is in mating contact with a complimentary profiled section of the second transmission member.

20. The torque limiting device of aspect 19, wherein the profiled section of the first transmission member comprises flexible portions which slip or cam over the complimentary profiled section of the second transmission member once a predetermined torque has been reached.

21. A torque limiting device, comprising:
a handle;
a drive shaft attached to the handle;
a torque limiting assembly coupled to the drive shaft;
the torque limiting assembly further comprising an expansion sleeve having a first end facing the handle and a second end facing away from the handle;
an adjusting sleeve surrounding the expansion sleeve
a shaft element with a camming member,
wherein the expansion sleeve further comprises a plurality of legs facing towards the second end and being elastic radially with regard to an axis of longitudinal extension of the expansion sleeve, and wherein the camming member interacts with the radially flexible legs of the expansion sleeve.

22. A torque limiting assembly for insertion into a torque limiting device, the torque limiting assembly comprising:
an expansion sleeve having a first end and a second end;
an adjusting sleeve surrounding the expansion sleeve
a shaft element with a camming or transmission member,
wherein the expansion sleeve further comprises a plurality of legs facing towards the second end and being elastic radially with regard to an axis of longitudinal extension of the expansion sleeve, and wherein the camming or transmission member interacts with the radially flexible legs of the expansion sleeve, and
wherein the first end of the expansion sleeve is designed to be coupled to a drive shaft of a torque limiting device.

23. A method to assemble a torque limiting assembly, the method comprising the steps of:
providing an expansion sleeve with a first end and a second end, the expansion sleeve comprising an opening at the second end and an upper opening at the first end, and further comprising an outer thread on an outer surface;
providing a shaft element with a first end and a second end, the shaft element comprising an enlargement portion;
inserting the shaft element into the expansion sleeve in longitudinal direction with its the first end through the opening of the second end of the expansion sleeve and putting the first end through the upper opening of the expansion sleeve;
fixing the shaft element in the upper opening in longitudinal direction;
providing an adjusting sleeve with an inner thread;
slipping the adjusting sleeve over the expansion sleeve; and
coupling the adjusting sleeve to the expansion sleeve by means of the outer and inner threads.

I claim:
1. A torque limiting device, comprising:
a handle;
a drive shaft attached to the handle;
a torque limiting assembly coupled to the drive shaft;
the torque limiting assembly further comprising
a shaft element having a first end and a second end;

a first transmission member attached to the first end of the shaft element, the shaft element is disposed within the first transmission member;

a second transmission member being fixed to the second end of the shaft element and interacting with the first transmission member; and an adjusting sleeve for adjusting a degree of interaction between the first transmission member and the second transmission member, the adjusting sleeve being slipped over the first transmission member and rotatably adjustable on the first transmission member by being rotatably mounted onto an outer thread on the first transmission member.

2. The torque limiting device of claim 1, wherein the first transmission member comprises a profiled section which is in mating contact with a complementary profiled section of the second transmission member.

3. The torque limiting device of claim 2, wherein the profiled section of one of the first or the second transmission members comprises flexible portions which slip or cam over the complementary profiled section of the respective other one of the first transmission member or the second transmission member once a predetermined torque has been reached.

4. The torque limiting device of claim 1, wherein the first transmission member extends outside the adjusting sleeve.

5. The torque limiting device of claim 1, wherein the first transmission member is an expansion sleeve, and wherein the second transmission member is a portion of the shaft element housed within the first transmission member.

6. The torque limiting device of claim 5, wherein the expansion sleeve comprises a first end and a second end, and further comprises a plurality of legs extending towards the second end and being elastic radially with regard to an axis of longitudinal extension of the expansion sleeve.

7. The torque limiting device of claim 6, wherein the second transmission member is a camming member interacting with the legs of the expansion sleeve.

8. A torque limiting assembly for insertion into a torque limiting device, the torque limiting assembly comprising:
a first transmission member;

a shaft element with a first end and a second end, the first end of the shaft element is attached to the first transmission member, a second transmission member attached to the second end of the shaft element and interacting with the first transmission member, the shaft element is disposed within the first transmission member; and an adjusting sleeve for adjusting a degree of interaction between the first transmission member and the second transmission member, the adjusting sleeve being slipped over the first transmission member and rotatably adjustable on the first transmission member by being rotatably mounted onto an outer thread on the first transmission member.

9. The torque limiting device of claim 8, wherein the first transmission member comprises a profiled section which is in mating contact with a complementary profiled section of the second transmission member.

10. The torque limiting device of claim 9, wherein the profiled section of the first transmission member comprises flexible portions which slip or cam over the complementary profiled section of the second transmission member once a predetermined torque has been reached.

* * * * *